United States Patent [19]

Corey

[11] Patent Number: 4,813,602

[45] Date of Patent: Mar. 21, 1989

[54] PULSATING LIQUID CLEANING DEVICE

[76] Inventor: Paul Corey, 13550 Nogales Dr., Del Mar, Calif. 92014

[21] Appl. No.: 137

[22] Filed: Jan. 2, 1987

[51] Int. Cl.⁴ .............................................. B05B 1/08
[52] U.S. Cl. .................................. 239/101; 222/246; 222/387; 239/331; 433/90
[58] Field of Search ................. 239/99, 101, 331, 380; 433/80, 90; 128/65, 66; 222/246, 387

[56] References Cited

U.S. PATENT DOCUMENTS

| | | | |
|---|---|---|---|
| 723,822 | 3/1903 | Buchanan | 433/90 |
| 852,065 | 4/1907 | Keller | 239/331 |
| 2,022,021 | 11/1935 | Wheeler | 141/1 |
| 2,039,177 | 4/1936 | MacKenzie | 221/47 |
| 2,556,517 | 6/1951 | Broussard | 299/25 |
| 3,362,401 | 1/1968 | Fainman | 239/1 |
| 3,507,275 | 4/1970 | Walker | 239/101 |
| 3,561,433 | 2/1971 | Kovach | 128/66 |
| 3,576,294 | 4/1971 | Baldwin | 239/101 |
| 3,739,983 | 6/1973 | Jousson | 239/101 |
| 3,809,298 | 5/1974 | Harris, Sr. et al. | 239/331 |
| 3,810,465 | 5/1974 | Lambert | 128/66 |
| 3,902,664 | 9/1975 | Deines | 239/99 |
| 4,022,350 | 5/1977 | Amron | 222/79 |
| 4,101,075 | 7/1978 | Heitzman | 239/101 |
| 4,489,750 | 12/1984 | Nehring | 137/496 |
| 4,512,514 | 4/1985 | Elcott | 239/99 |

*Primary Examiner*—Andres Kashnikow
*Assistant Examiner*—Michael J. Forman
*Attorney, Agent, or Firm*—Brown, Martin, Haller & Meador

[57] ABSTRACT

A cleaning apparatus for generating a pulsed liquid stream, comprising a fluid tight housing having a cylindrical side wall, and first and second ends being compact enough to be hand held by a user. A piston mounted in the housing forms a liquid tight seal with the sides of the housing and slides between a first and a second position in response to an actuation means operated by hand pressure. An output port in the second end of the housing is connected to a nozzle for directing liquid at a desirable location. A liquid control means connected between the output port and the nozzle receives pressurized liquid exiting through the output port and transfers discrete portions of the liquid to the nozzle forming a pulsative stream of liquid exiting the nozzle.

The liquid control means can comprise a rod connected to the piston and extending toward the output port with a plurality of cylindrical plugs secured thereto at intervals determined by a desired length or fluid quantity for pulses in said pulsative stream, each plug having a length commensurate with desired periodicity for pulses in said pulsative stream, and a diameter as close to that of said output port as possible without preventing the movement through the output port.

In addition, a liquid tight, flexible or static bladder for confining predetermined portions of a desired cleaning solution can be employed within the apparatus housing.

7 Claims, 2 Drawing Sheets

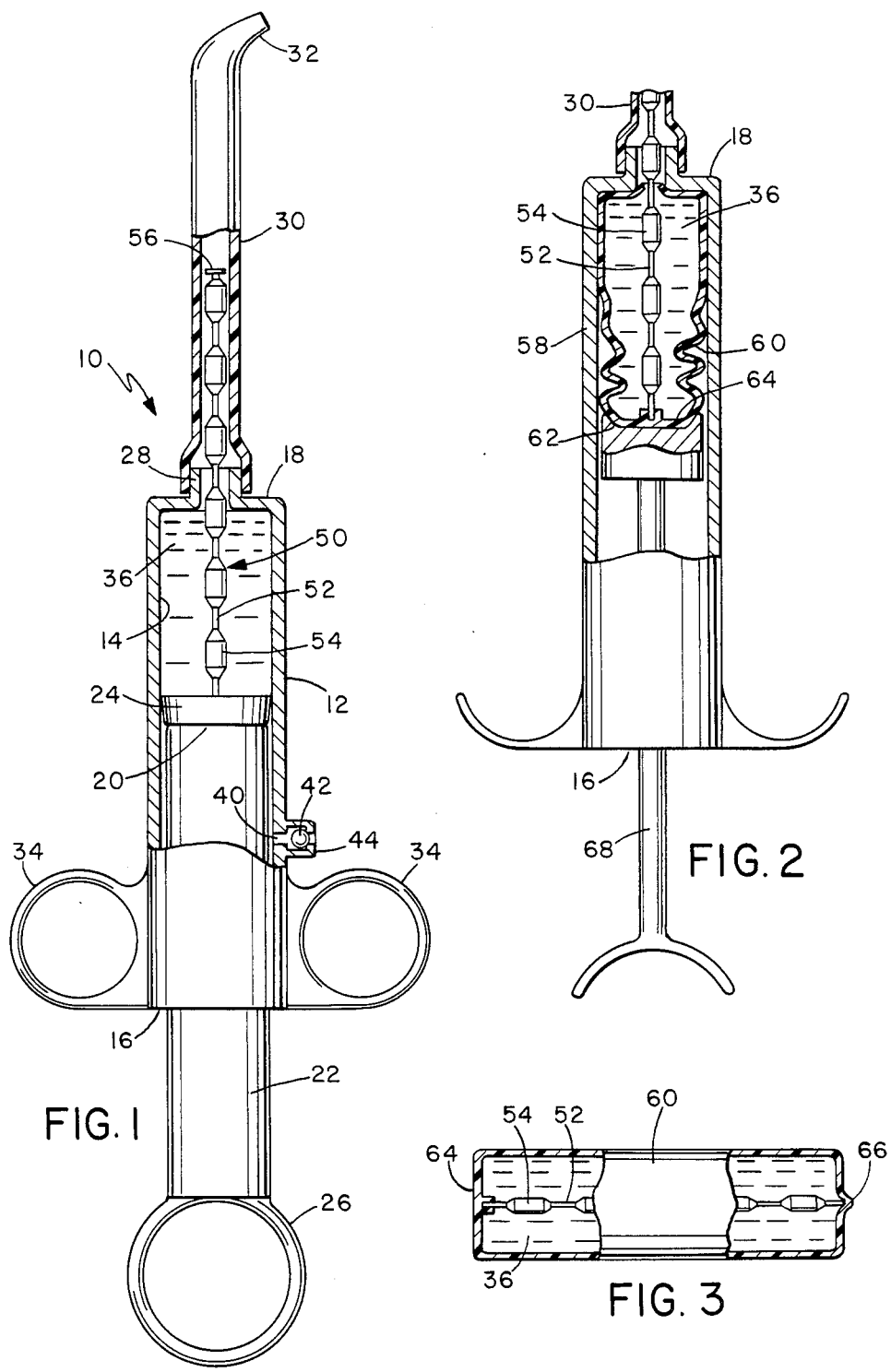

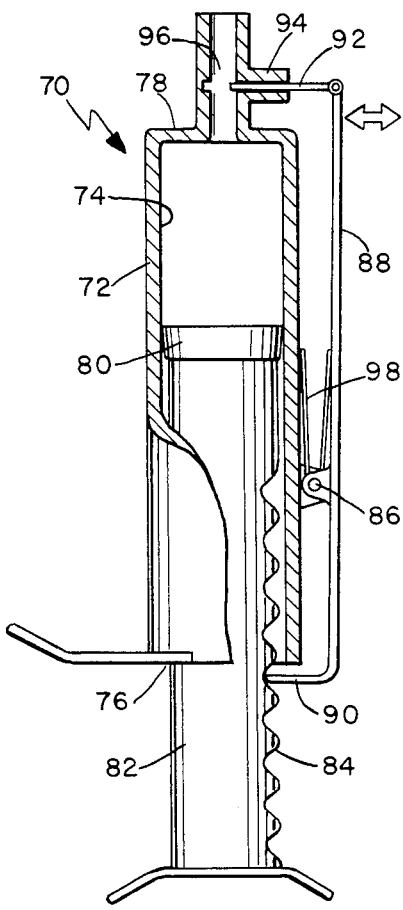
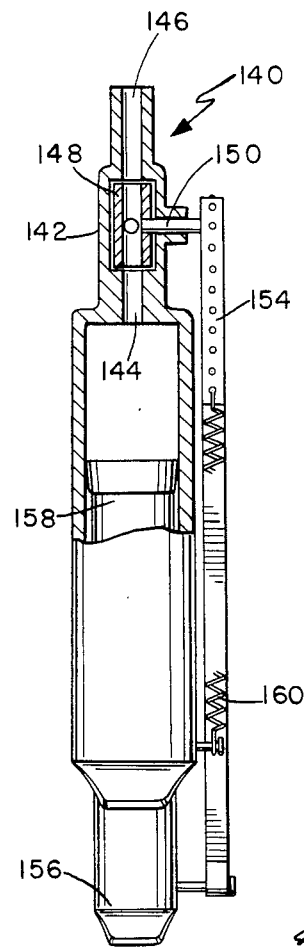
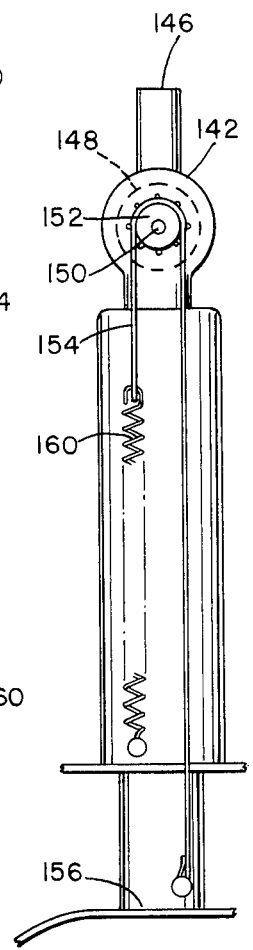
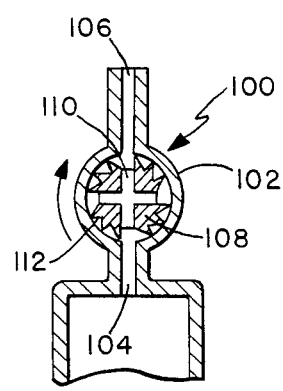
FIG. 4
FIG. 6
FIG. 7
FIG. 5

PULSATING LIQUID CLEANING DEVICE

BACKGROUND OF THE INVENTION

1. Field of the Invention

The present invention relates to directed fluid cleaning apparatus and more particularly to a portable apparatus for providing intra-oral pulsating liquid jets for dental hygiene purposes. The invention further relates to pulsating liquid valves coupled to an output port of a liquid reservoir comprising a cylindrical enclosure and manually operable piston combination.

2. Background

There are many applications where it is desirable to remove small amounts of material or debris from crevices and small confined volumes in order to provide a "clean" surface. One such application is in the area of dental hygiene where it is necessary to remove food debris to reduce acidity and plaque formation.

Floss and brush and paste combinations have been the traditional tools for cleaning teeth and providing proper dental hygiene. However, even with great care these tools have failed to address all of the periodontal needs of the user. Most notably, brushing and flossing are generally inadequate for cleaning the root portions of teeth adjacent to gums and other tissue. This gives rise to decay and several forms of periodontal disorders. While some advance has been gained in alternate brushing techniques to improve cleaning, a normal toothbrush can in fact damage the thinner tooth enamel in the root area if used excessively. The application of floss to lower tooth areas proves very difficult and time consuming for most users, which dissuades long term use.

The primary alternative has been frequent visits to a dentist where specialized high speed brushes and cleansing compounds are used for cleaning and removing built up plaque and debris. However, this is a time consuming, expensive, and inadequate approach in terms of prevention of the onset of decay. Therefore, there has been a long standing need to develop improved, easy to use, tools or techniques for daily dental hygiene to provide preventative care for a user.

In response to this need, a new technique involving pulsed water jets was developed to remove material from between teeth and some dental work structures. One such device is described in U.S. Pat. No. 3,576,294 issued to W. B. Baldwin in Apr. 27, 1971. This patent discloses a cleansing device which utilizes a pressurized liquid in a reservoir which is then pumped up through a series of valves and out through a nozzle. The device is constructed so that liquid is pumped in discrete pulses which offers an improved method of cleansing the teeth and gums of a device user. Other devices have been developed to improve upon the spray nozzle and to provide massaging effects for the gums. One such device is U.S. Pat. No. 3,739,983 issued to P. J. Jousson on June 19, 1973.

However, these devices rely on electrically powered pumps to create pulsed liquid streams. The electric motors represent a safety problem and require specialized grounding and seating techniques to decrease or prevent the hazard of shock in a bathroom area where the device is typically used. In addition, the use of an electric motor means that the device is limited to use in a fixed household location having an electric outlet.

The present pulse liquid devices also utilize small basins to hold water or other cleansing liquids which require O-ring seals, clamps and other structures to interface with the electric pump. Plastic tubing or other liquid conductors are required to transfer the liquid to a nozzle tip which is used to direct the liquid into the users mouth. This results in a strong and useful, but totally inflexible and immobile liquid jet cleaning system. It is necessary to keep all of the interlocking and interfacing pieces clean from any build up of sediment, as present in many hard water systems, or other debris in order to keep them functioning properly. All of the parts and pieces required to compose such a system also take up a rather significant amount of room which can be excessive for a small bath area. All of these features result in a device that is chiefly inconvenient and not portable.

Since proper dental hygiene is equally, if not more so important, when a person is constantly traveling or in remote locations, it would be an improvement in the art to have a pulsating liquid dental cleansing device that is portable. In addition, it would be extremely desirable to provide a dental hygiene cleansing system which is easy to use and maintain, or even disposable.

The drawbacks, such as portability, size, and complexity, in dental cleaning applications are also found in other cleaning applications. Therefore, it is also desirable to have a compact, portable, and possibly disposable, liquid dispensing cleaning apparatus.

SUMMARY

Therefore, it is an object of the present invention to provide an apparatus which produces a pulsating stream of liquid for removing debris and particles from confined volumes and crevices.

It is another object of the present invention to provide an apparatus which generates pulsating liquid streams for use as a dental hygiene tool that is very lightweight and portable.

It is a purpose of the present invention to provide an apparatus which generates a pulsating, cleansing liquid stream for use as a dental hygiene tool that does not require or rely on an electrical power source.

It is a further purpose of the present invention to provide an apparatus that generates a pulsating liquid stream from liquid stored in a reservoir utilizing a pulsating valve.

These and other purposes, objects, and advantages are realized in a cleaning apparatus for generating a pulsed liquid stream, comprising a fluid tight cylindrical housing having a side and first and second end walls. The housing is made from materials such as, but not limited to, stainless steel, a high impact translucent plastic, or an autoclavable material and is compact enough to be hand held by a user. A piston mounted in the housing forms a liquid tight seal with the sides of the housing and slides between a first and a second position in response to an actuation means operated by hand pressure. A first output port in the second end of the housing is connected to a nozzle for directing liquid at a desirable location. A liquid control means connected between the output port and the nozzle receives pressurized liquid exiting through the output port and transfers discrete portions of the liquid to the nozzle forming a pulsative stream of liquid exiting the nozzle.

In one aspect of the present invention, the first output port comprises a circular port having a diameter determined by the pressure and amount of liquid flow desired and the liquid control means comprises a rod connected to the piston and extending toward the output port with a plurality of cylindrical plugs secured thereto at intervals determined by a desired length or liquid quantity for pulses in the pulsative stream, each plug having a length commensurate with a desired periodicity for pulses in the pulsative stream, and a diameter as close to that of the output port as possible without preventing the movement through the first output port.

In addition, a liquid tight, flexible or static bladder small enough to allow insertion into the housing of the cleaning apparatus can be employed for confining predetermined portions of a desired cleaning solution. The flexible bladder is formed from a readily deformable material and has a bottom wall with a depression which automatically aligns the bottom wall with the output port and a top wall with means for holding one end of the valve rod.

In further aspects of the invention, the fluid control means comprises a cylindrical main control means housing with a central longitudinal axis extending transverse to the direction of liquid flowing from said first output port and a predetermined inside diameter; an input port; a second output port; and a rotating control valve disc. The rotating disc is rotatably mounted within the control means housing and has a diameter smaller than the housing so as to allow rotation about a central disc axis which is substantially coextensive with the main housing central axis. At least two passages extend through the control disc along a diameter and perpendicular to each other and to the central disc axis. The rotating disc can be mounted on an axle which extends on at least one end through a wall of the main control means housing where it is coupled to an external drive wheel. A drive chain coupled to the piston actuation means interacts with and rotates the drive wheel.

Alternatively, the main control means housing is spherical and employs a rotating control valve sphere with a diameter smaller than the main control housing so as to allow rotation. The rotating control sphere is rotatably mounted within the control means housing about a central spherical axis which is substantially aligned parallel to the direction of flow of liquid from said first output port. The control sphere has a plurality of grooves extending across an outer surface between a position adjacent the input port and a position adjacent the output port in a serpentine pattern.

BRIEF DESCRIPTION OF THE DRAWINGS

The novel features of the present invention may be better understood from the accompanying description when taken in conjunction with the accompanying drawings, in which like characters refer to like parts and in which:

FIG. 1 is a sectional view of a manually operated cleaning apparatus constructed according to the principles of the present invention;

FIG. 2 is a sectional view of a second cleaning apparatus according to the present invention and using an inserted liquid confining bladder;

FIG. 3 illustrates further details of the bladder of FIG. 2;

FIG. 4 is a sectional view of a special control valve for use in the present invention;

FIG. 5 is a sectional view of a rotating disc valve for use in the present invention;

FIG. 6 is an external drive mechanism for a rotating valve used in the present invention; and FIG. 7 is a side view of the drive mechanism of FIG. 6.

DETAILED DESCRIPTION OF PREFERRED EMBODIMENTS

The present invention comprises an apparatus for generating a pulse liquid stream for use in removing unwanted debris or particles from crevices or other confined volumes. The invention is specifically useful for generating a pulsed liquid stream for use as a dental hygiene tool. The generation of a pulsed liquid stream is accomplished using a piston and cylinder combination coupled to an output port having a nozzle for directing a stream of liquid at a desired location.

A liquid suitable for a desired cleansing application is placed in the cylinder and the piston manually actuated to pressurize the liquid and force it out of the output port and through the nozzle. A specialized liquid control means is connected between the output port of the cylinder and the nozzle for receiving liquid exiting from the port and transferring discrete portions of the liquid into the nozzle so as to form a discontinuous stream of liquid pulses. The apparatus is small and compact enough to be hand held and operated by digital manipulation so as to generate one or more pulsed liquid streams without electrical power or energy sources.

A pulsating cleaning apparatus constructed according to the principles of the present invention is illustrated in FIG. 1. In FIG. 1, a pulsed liquid cleaning apparatus 10 is illustrated using a liquid tight housing 12 having a generally cylindrical side wall 14 and first and second ends 16 and 18, respectively. The housing 12 can comprise a variety of materials such as stainless steel, glass or plastic. A translucent plastic is preferred for disposable applications due to ease and low cost of manufacture Stainless steel or plastic may be satisfactory for home use while glass or autoclavable plastics are generally preferred in dental office usage.

The first end of the housing 12, labeled 16, is referred to as the top end of the housing and is open for accepting a piston actuation means. While a preferred embodiment is illustrated in FIG. 1, it is not necessary that the end 16 be totally open but can partially enclose the area immediately adjacent to a piston actuator 22 which occupies a small portion of the opening.

Positioned within the enclosure 12 is a piston 20 coupled to the piston actuator 22. The outer diameter of the piston 20 is approximately the same as the inner diameter of the cylindrical enclosure 12. The piston 20 needs to form a slidable but liquid tight seal between the outer perimeter of the piston 20 and the cylindrical side wall 14. To aid this sealing process, it is possible to use a separate seal 24 positioned about the diameter of the piston 20 which can comprise an O-ring, or another flexible rubber member. In the alternative, the end of the piston 20 can comprise a large expanded rubber member whose diameter is manufactured to be slightly larger than the inside diameter of the enclosure 12.

The piston actuator 22 extends out of the enclosure 12 through the open end 16 where it terminates in a handle 26. The handle 26 comprises a circular loop or ring through which an individual's thumb or finger may be inserted in order to hold the actuator 22 and manually manipulate the actuator and, thus, the piston 20 within the enclosure 12. It is not necessary that the handle 26 completely enclose the digit that is used to actuate the piston 20. In fact, the handle portion of the piston actuator 22 can terminate in a substantially flat stub for those applications where a single activation of the piston 20 will be used, such as in disposable applications.

The closed end 18 of the housing 12 has a port 28 through which liquid can escape from the housing 12 and enter into a nozzle 30. The nozzle 30 is a long thin tube-like structure having a central longitudinal axis and having a narrower diameter portion on one end which is bent at an angle to the central axis to form a narrow tip 32 for projecting a liquid stream at an angle to the main nozzle body 30. The nozzle 30 is preferably attached to the port 28 so that it can be rotated at least slightly to vary the direction of a liquid stream relative to the position of the piston handle 26 or a hand operating the apparatus 10. This can be accomplished by terminating the end of nozzle 30 where it attaches to the port 28 with a cylindrical side wall having a slightly larger diameter than the port 28 output. However, for disposable applications the nozzle 30 may be secured in place by various adhesives or otherwise molded as part of the housing 12 so as to form a unitary structure.

The liquid cleaning apparatus 10 functions in the manner similar to a common syringe wherein liquid within the housing 12 is expelled through the port 28 and the nozzle 30 in response to pressure from piston 20 which is actuated by the actuator 22. In order to assist in grasping the liquid cleaning device 10, finger grips or similar handles 34 may be provided along the outside of the side wall 14.

The liquid cleaning device 10 is generally filled with a cleaning liquid 36 whose composition is determined by the specific cleaning application desired. Clear water may be sufficient for some applications while specialized chemical compositions may be preferred for other applications. There are a number of cleaning liquids known in the dental arts for providing cleaning and plaque inhibiting actions when applied to the teeth. When the liquid cleaning device is used in connection with cleaning small parts or machinery, there are a number of solvents that are known in the machine arts for providing degreasing and cleaning actions. Therefore, those skilled in the art to which the particular application of the liquid cleaning device 10 pertains will readily know or understand the cleaning liquid 36 to be used.

The liquid cleaning device 10 may be prefilled with cleaning liquid 36 as when manufactured in a factory situation for predetermined cleaning applications. In the alternative, the liquid cleaning device 10 may be filled by the perspective user by exerting upward pressure on the piston actuator 22 so as to slide the actuator 22 and thus, the piston 20, toward the open end 16 of the enclosure 12 while holding the nozzle 30 in a container of the appropriate cleaning liquid 36. An alternate method of disposing cleaning liquid 36 within the enclosure 12 is to provide an input port 40 in the cylindrical side wall 14 through which liquid may be poured. If the input 40 is located along the cylindrical side wall 14 toward the open end 16, then a sufficient amount of cleaning liquid 36 will remain in enclosure 12 when the piston 20 is moved along the cylindrical side walls after filling.

In order not to worry about any expulsion of extra cleaning liquid, nor the hazards and mess associated with an open input port 40, an actuator mechanism such as a small ball 42 in a housing 44 can be provided, which allows the flow of liquid into the enclosure 12 but impedes the flow of cleaning liquid 36 out of the housing 12 when pressure is applied.

The cleaning liquid 36 expelled out of the enclosure 12 and through the nozzle 30 will be under a certain amount of pressure as determined by the area of the piston 20 and the size of the opening through port 28. However, what has been described at this point is a continuous stream of pressurized liquid exiting the nozzle 30. In order to form a pulsative stream of liquid 36, a liquid control mechanism 50 is disposed within the liquid cleaning device 10.

In the preferred embodiment illustrated in FIG. 1, the liquid control mechanism 50 comprises a thin rod 52 on which is disposed a series of plugs 54. The plugs 54 are made to have an outside diameter very close to the inside diameter of the port 28. This is done in order to block as completely as possible the escape of liquid and displace any liquid 36 where the plug is residing within the port 28 The length of the plugs 54 is determined by the desired spacing between pulses of liquid escaping from the nozzle 30. The spacing of the pulses is in turn determined by the average frequency desired for the liquid stream striking the area to be cleaned.

Those skilled in the art understand the general guidelines for using pulsed streams of liquid for cleaning and guidelines have been developed for the periodicity required for the pulses. From a desired periodicity and/or frequency for the liquid stream the periodic spacing required between liquid pulses is readily computed. This spacing is then translated into the length required both for the spacing between the plugs 54 and the length of the plugs themselves. In general, the spacing between the plugs will probably be slightly larger than the length of the plugs since the pulse width of the cleaning liquid is generally greater than the pulse separation.

The rod 52 should be made from a reasonably strong, yet flexible, material to allow for movement and turns within the enclosure 12, the port 28, and the nozzle 30. The length of the rod 52 is determined by the fact that it can be no shorter than the maximum allowable separation between the piston 20 and the opening of the port 28 in order to prevent misalignment of the rod into the enclosure 12 where it can become jammed and even broken when the actuator 22 is pressed upon. At the same time, the rod 52 should be no longer than the distance from the bottom of the piston 20 when it is in contact with the closed end 18 and the end of the nozzle 30 where it bends to form the tip 32. If the rod 52 is made any longer it will strike the end of the nozzle 30 causing damage to the nozzle 30 and the rod 52.

In operation, cleaning liquid 36 is placed in the chamber formed by the cylindrical side walls 14 in the enclosure 12 and pressurized by the piston 20 and forced out through output port 28 and nozzle 30. While the cleaning liquid 36 is exiting through the port 28, the plugs 54 moving along with the motion of the piston 20 cause alternating discontinuities in the flow of liquid 36 which creates an alternating pressurized liquid stream flowing into the nozzle 30 and thus, out of the nozzle tip 32 and onto an area being cleaned.

The above described embodiment provides an advancement in the art of dental hygiene in that a portable hand held dental cleansing tool is provided which requires no external power source, nor liquid pressurizing apparatus. However, as described above, the cleaning device 10 utilizes a liquid reservoir within the enclosure 10 which must be filled from an external source by the user or prefilled at a factory. For disposable applications a prefilled enclosure 12 is preferred. However, filling of the apparatus 10 by an individual user may prove to be somewhat messy and unduly complicated for younger aged users. Therefore, an alternate embodiment is illustrated in FIG. 2 utilizing a pre-measured bladder type reservoir.

In FIG. 2, the enclosure 58 has the same open and closed ends 16 and 18, respectively, and utilizes an output port 28 and nozzle 30 as previously described. However, the cleaning liquid 36 is contained in a bladder 60 which is inserted into the enclosure 58.

The bladder 60 comprises a generally cylindrical container formed from a strong, but flexible material such as a thin polyethylene plastic. The bladder 60 my be manufactured by methods such as electrodeless welding or injection molding and is considered within the understanding of manufacturing techniques typically used in the plastics arts. The bladder 60 is prefilled with a predetermined amount of cleaning liquid 36 which is designated by the type of cleaning application desired. In this manner, a variety of predetermined dosages or types of liquid may be used by a common liquid cleaning device without complicated filling or cleaning schemes. The advantage of this technique is that children or younger users may employ a flavored cleaning liquid or a smaller quantity of cleaning liquid for dental hygienic purposes while adults would be employing a larger dose. At the same time, different types of cleaning liquids can be used, some having plaque retardants and others without, depending upon the personal preference of the user.

Provided that the walls of the bladder 60 are comprised of fairly flexible versus static material, it will collapse as a piston 62 presses down on top of it forcing liquid 36 out through the port 28 until the bladder is substantially collapsed toward the closed end 18 of the enclosure 58.

Alternatively, the bladder 60 comprises a fairly rigid, static rather than flexible, material. In this application the bladder 60 has a cylindrical sidewall which fits inside of the enclosure 20 and contains a piston 20 mounted to slide along the bladder sidewall. The piston 20 employs a threaded hole or similar fastening means to which the valve actuator 68 will be secured. The use of a less flexible bladder or insert structure may decrease damage due to puncture or rupture for some travel situations.

In order to provide for the pulsed stream as previously described, the rod 52 with plugs 54 mounted thereon is premounted inside the bladder 60. This may be accomplished by attaching the rod 52 to an upper end 64 of the bladder 60 which faces a piston 62. The end 64 of the bladder can have a region which is a substantially thicker plastic material to which the rod 52 may be attached or even a small metallic insert to which the rod may be attached, depending upon the specific material such as plastic versus stainless steel that the rod 52 is constructed from. In the case of a static bladder employing an inserted piston, the rod 52 can be secured directly to, or formed as part of, the piston.

On the opposite end of the bladder 60 from end 64 is a slight depression 66 which is intended to mate with the depression naturally formed in the closed end 18 by the output port 30. Such a depression, being premolded in the bladder 60, aligns the end of the bladder 60 and the projecting rod 52 with the port 30.

As illustrated in FIG. 3, the end of the rod 52 is captured by the sides of the depression 66 which align it with the port 30. In addition, or in the alternative, the end of the rod 52 may be encapsulated in the plastic material forming the side of the bladder 60 near the end of the depression 66. This latter technique is a preferred embodiment because it allows the automatic attachment of the rod 52 to the end 64 of the bladder 60. The bladder 60 is filled through an opening in the depression 66 and then the end wall of the depression 66 sealed to encapsulate the liquid and imbed the end of the rod 52 therein. This approach allows for automatic alignment of the rod 52 which will penetrate through the end wall of the depression 66 allowing liquid to escape from the bladder 60 and into the nozzle 30.

When using a bladder 60, the piston 62 may be less complex and need not provide a liquid tight seal as the piston 62 and can also utilize a thinner piston actuator 68. While the rod 52 and plug 54 valve assembly or liquid control mechanism of the embodiments described herein provide an advance in the art of pulsed liquid cleaning, other embodiments are possible for controlling the flow of pressurized liquid 36.

FIGS. 4–7 illustrate alternate embodiments for a fluid control means constructed according to the principles of the present invention and operable in connection with an output port for generating pulsative liquid 36 streams.

In FIG. 4, a cleaning apparatus 70 is illustrated as having an enclosure 72 with side wall 74 with open and closed ends 76 and 78, respectively, and a piston 80 moved by a specialized piston actuator 82. Along one side of the actuator 82 is a series of teeth or depressions 84 that alternate between two heights. Viewed in the alternative, the actuator 82 may have an exterior diameter that varies between a predetermined minimum and maximum value along its length.

Attached to the exterior portion of the cleaning apparatus 70 housing 72 is a fulcrum point 86. A valve lever arm 88 is pivotally attached to the housing at the fulcrum point 88 so as to be able to freely rotate about this point. On an upper end of the valve arm 88, adjacent to the open end of the housing, is a projection 90 for engaging the teeth 84 on the actuator 82. As the actuator 82 is moved up and down within the enclosure 72, the teeth 84 interact with the projection 90 to move the valve arm 88 back and forth with respect to the side of the housing 72.

On the opposite end of the valve arm 88 is a valve pin 92 which extends through a valve seat opening 94 in a port 96. As the actuator 82 is moved up and down within the housing and causes the valve arm 88 to move back and forth, the valve pin 92 likewise moves in and out of the port 96 region through the valve seat 94. If desired for smoother operation, the valve pin 92 can be pivotally mounted on the lever arm 88.

A spring 98 positioned between the side of the housing 72 and the lower end of the valve arm 88 forces the valve arm 88 to move away from the side of the housing and thus, the valve pin 92 to move out of the valve seat opening 94. It is the pressure of the teeth 84 against projection 90 that forces the valve arm 88 to rotate in the opposite direction against the spring 98 and push the valve pin 92 back into the port 96 region. It is this alternating motion of the valve pin 92 in and out of the valve seat opening which interacts with cleaning liquid 36 escaping from the enclosure 72 causing variations in the pressure of the liquid 36 and producing a pulsative liquid stream.

FIGS. 5-7 illustrate the application of specialized revolving turbine valves adjacent to the output port of a cleaning apparatus constructed according to the principles of the present invention.

In FIG. 5 pulsating turbine valve 100 is illustrated having a housing 102, an input port 104 and an exit port 106. The input port 104 is coupled to an output port 30, not shown, for an enclosure 12 and the exit port 106 couples to a nozzle 30 as previously discussed. The housing 102 is substantially circular when viewed in one direction and substantially planar when viewed at a right angle thereto.

A turbine rotor 108 is positioned within the turbine valve enclosure 102 and has a substantially circular disc shape with an external diameter slightly smaller than the internal diameter of the housing 102. The turbine rotor 108 has two liquid passages 110 positioned at right angles to each other and connecting opposite sides. The liquid passages 110 allow the flow of cleaning liquid 36 from one side of the turbine rotor 108 to the other when aligned between the input port 104 and exit port 106.

In order to provide a pulsative effect on the liquid stream flowing through the turbine valve 100, a series of flexible turbine fins 112 are disposed along the circumference of the turbine rotor 108. By making the diameter of the turbine rotor 108 smaller than the inside diameter of the enclosure 102 and then filling that difference with the flexible turbine fins 112, liquid can attempt to flow around the rotor 108 rather than through the passages 110. In order to aid in the deflection of liquid, the passages 110 are made smaller than the diameter of output port 30 for the enclosure 12. Therefore, more liquid tries to flow through the passages than reasonably can, building up sufficient pressure behind the opening to the passages 110 and causing liquid to attempt to flow around the turbine disc.

As liquid attempts to flow around the rotor disc 108 and catches against the turbine fins 112, the disc 108 begins to rotate. As the rotor rotates slightly, the liquid passages 108 become blocked as to a direct path between the input and output ports 104 and 106, respectively, causing more liquid to be deflected, thus, causing the disc to rotate even more. At some point the turbine rotor will reach an optimum rotating speed in which sufficient liquid is flowing past passages 110 versus a predetermined amount of liquid flowing through the passages 110. When a point of equilibrium is reached, a pulsating stream of liquid is generated at the output port 106 which is transferred into the nozzle 30.

An alternate valve rotor 108 comprises a spherical ball shaped rotor having a series of parallel, spaced apart channels extending across the surface in an "S" shaped configuration. Each channel begins and terminates at positions that are offset, in opposite lateral directions, from a central spherical axis. By positioning the input and output ports in alignment with the channel ends, fluid traveling therethrough is pulsed through the output port as the rotor rotates. Rotation results from pressure exerted on the curved sides of the channels by cleaning fluid trying to flow in a straight line and being deflected by the channel sides. The pressure turns the spherical rotor which causes channels to periodically connect input and output ports and generate the desired pulsating stream of cleaning fluid through the valve.

FIGS. 6 and 7 illustrate an additional embodiment for activating a revolving pulsative valve utilizing external mechanical forces to cause valve rotation. In FIGS. 6 and 7, a rotating valve assembly 140 is illustrated having a valve housing 142 with an input port 144 and output port 146 coupled between an output port of a cleaning apparatus housing 122 and an output nozzle.

Inside the valve housing 142, which can be substantially spherical or planar depending on the desired application, resides a rotating valve disc or ball rotor 148. The valve rotor 148 has a pin or axle 150 positioned along a central axis that extends outward from one surface of the rotor to contact the inner walls of the enclosure 142. This pin acts as an axle on which the valve rotor 148 freely rotates. For added stability, the axle 150 is long enough to extend out both sides of the rotor 148 and contact opposite sides of the housing 142. Alternately, two separate pins or axle pieces are used to form the axle 150.

As shown in FIG. 6, one end of the axle 150 extends out through a sidewall of the housing 142 where it is coupled to a geared or toothed disc 152. The geared disc 152 is configured to interact with a chain or driving member 154 which extends from the rotating valve 140 along the side of the enclosure 122 to a handle 156 of a valve actuator 158. One end of the chain 154 is attached directly to the actuator 158 adjacent to the handle 156. The other end of the chain 154 is attached to a retraction spring 160 which is in turn attached to the housing 122 adjacent the actuator 158. The chain 154 can comprise a variety of devices for interacting with a wheel or pulley member and cause it to rotate. A preferred apparatus comprises a thin belt of plastic material having slots or holes disposed along its length. Such a drive "chain" is lightweight, easy to keep clean, and safe around children. The wheel 152 comprises a disc having raised "fingers" or bumps for engaging the slots or holes and being moved by the chain 154. Alternately, a plastic rope having spherical beads of material disposed at intervals along its length could be used in combination with a disc having mating spherical depressions about its periphery. However, metal chains or cogged wheels, as known in the mechanical arts, can also be employed.

For the embodiment of FIGS. 6 and 7, the valve actuator 158 is slowly withdrawn from the housing 122 while the port 146 is directly, or indirectly, exposed to the desired cleaning liquid. This fills the housing for use. As the handle 156 is pulled away from the housing 122 it pulls on the chain 154 and against the spring 160 which extends. During use of the cleaning apparatus, the actuator 158 is moved down into the enclosure 122 and the chain 154 is pulled on by the retraction spring 160 so that it moves down around the gear disc 152 and along the side. This causes the geared disc 152 to rotate which in turn rotates the valve disc 148. Passages through the valve disc 148 then alternately allow the passage of pressurized liquid out of the enclosure 122 and into the nozzle.

What has been described then is a new type of cleaning apparatus especially useful as a dental hygiene tool which provides directed pulsed liquid streams of cleaning fluids into small or confined volumes. The cleaning apparatus does not require external or auxiliary power sources but is manually operated. In addition, other types of cleaning applications will benefit from the apparatus.

The foregoing description of preferred embodiments has been presented for purposes of illustration and description. It is not intended to be exhaustive nor to limit the invention to the precise form disclosed, and many modifications and variations are possible in light of the above teaching. The embodiments were chosen and described to best explain the principles of the invention and its practical application to thereby enable others skilled in the art to best utilize the invention in various embodiments and with various modifications as are suited to the particular use contemplated. It is intended that the scope of the invention be defined by the claims and their equivalents.

What I claim is:

1. A cleaning apparatus for generating a pulsed liquid stream, comprising:
   a fluid tight housing having a cylindrical side wall, and first and second ends, being compact enough to be hand held and operated;
   a piston mounted within said housing and contacting said side wall so as to form a liquid tight seal therewith being slidable between a first position adjacent said first end and a second position adjacent said second end;
   piston actuation means connected to said piston for manually moving said piston in response to hand pressure, mounted to extend out of said housing on said first end for being contacted by a portion of a hand;
   an output port in said second end of said housing;
   nozzle means connected to said output port for directing liquid flow at a desirable location; and
   liquid control means connected to said piston and disposed between said output port and said nozzle means for receiving liquid exiting through said output port under pressure due to movement of said piston toward said second end and transferring discrete portions of said liquid to said nozzle means so as to form a pulsative stream of liquid exiting said nozzle means.

2. The apparatus of claim 1 wherein said output port comprises a circular port having a diameter determined by the pressure and amount of liquid flow desired and said fluid control means comprises:
   a rod connected to said piston and extending toward said output port being greater in length than a separation distance of said piston side from said second end;
   a plurality of solid cylindrical plugs secured to said rod at intervals determined by a desired length or liquid quantity for pulses in said pulsative stream, each plug having a length commensurate with a desired periodicity for pulses in said pulsative stream, an a diameter as close to that of said output port as possible without preventing the movement of said plugs through said port.

3. The apparatus of claim 2 wherein said housing comprises a cylindrical body comprising stainless steel.

4. The apparatus of claim 2 wherein said housing comprises a cylindrical body comprising high impact plastic.

5. The apparatus of claim 2 wherein said housing comprises a cylindrical body comprising an autoclavable material.

6. An apparatus for generating a pulsed liquid stream for use s a dental hygiene tool, comprising:
   a fluid tight housing having a cylindrical side wall, and first and second ends, being compact enough to be hand held and operated;
   a piston mounted within said housing and contacting said side wall so as to form a liquid tight seal therewith, being slidable between a first position adjacent said first ned and a second position adjacent said second end;
   piston actuation means connected to said piston for manually moving said piston in response to hand pressure, mounted to extend out of said housing on said first end for being contacted by a portion of a hand;
   an output port in said second end of said housing;
   nozzle means connected to said output port for directing liquid flow at a desirable location; and
   liquid control means connected to said piston and disposed between said output port and said nozzle means for receiving liquid exiting through said output port under pressure due to movement of said piston toward said second end and transferring discrete portions of said liquid to said nozzle means so as to form a pulsative stream of liquid exiting said nozzle means.

7. The apparatus of claim 6 wherein said housing comprises a cylindrical body comprising an autoclavable material.

* * * * *